United States Patent [19]

Bloom

[11] Patent Number: 4,478,825
[45] Date of Patent: Oct. 23, 1984

[54] WARM ETHANOL METHOD FOR PREPARATION OF LOW FIBRINOGEN ANTIHEMOPHILIC FACTOR

[75] Inventor: James W. Bloom, Bourbonnais, Ill.

[73] Assignee: Armour Pharmaceutical Company, Tarrytown, N.Y.

[21] Appl. No.: 542,243

[22] Filed: Oct. 14, 1983

[51] Int. Cl.³ .............................................. A61K 35/16
[52] U.S. Cl. .................................................... 424/101
[58] Field of Search ......................................... 424/101

[56] References Cited

U.S. PATENT DOCUMENTS 2,710,294  6/1955  Gerlough .............................. 260/122

Primary Examiner—Sam Rosen

[57] ABSTRACT

Antihemophilic factor (AHF), a blood protein component necessary for clotting of normal whole blood, is extracted and concentrated from a cryoprecipitate suspension containing AHF and fibrinogen as its principal components by: selectively precipitating fibrinogen from a water-ethanol solution and removing the ethanol therefrom.

18 Claims, No Drawings

WARM ETHANOL METHOD FOR PREPARATION OF LOW FIBRINOGEN ANTIHEMOPHILIC FACTOR

BACKGROUND OF THE INVENTION

1. Field of the Invention

This invention relates to a method of preparing antihemophilic factor (hereinafter called AHF, or Factor VIII) concentrate which is substantially fibrinogen free. AHF is a blood plasma protein useful for therapeutic administration to patients having hemophilia.

Hemostatis, the biochemistry of blood coagulation, is an extremely complex and as yet not completely understood phenomena whereby normal whole blood and body tissue prevent an excess loss of blood from a ruptured blood vessel. The total mechanism of blood coagulation is affected through the coordinated interaction of biochemical substances contained in three basic physiologic systems; namely, extravascular tissue such as subcutaneous tissue, muscle tissue, and skin; the blood vessel wall; and intravascular components, including blood plasma proteins, blood plasma factors, and platelets. By far the most important, and yet least understood, of the biochemical considerations affecting clotting, involve the intervascular blood components.

Since most of the blood clotting diseases in man occur in the intervascular blood system, usually due to a deficiency or inactivation of one or more blood plasma factors, great effort has been expended in this direction by scientific reasearch in an attempt to understand the role blood plasma factors play in the biochemical mechanism of blood clotting. Although in recent years much progress has been made in understanding the complexities of blood clotting, many more years of painstaking effort will be required before man finally gains sufficient knowledge to effectively ameliorate blood clotting disease. In the meantime, the state of the art with respect to the treatment of most blood clotting diseases will continue to be the administration of therapeutic pharmaceutical and biochemical substances in an attempt to relieve the adverse effects of these diseases.

A great deal of medical research into blood clotting diseases has been directed towards finding an acceptable treatment for hemophilia, a genetically induced disease characterized by the loss of clotability of otherwise normal whole blood. Although the precise cause of hemophilia is not known, one of the most popular theories suggests that it may be because of the absence of or a greatly inhibited presence of the active form of AHF in otherwise normal plasma from whole blood. At present, although hemophilia cannot be cured, it can often be treated therapeutically by the administration of AHF to an AHF-deficient individual. The administered AHF is derived from blood obtained from a normal and healthy donor. AHF is administered either by the transfusion of whole blood or blood plasma, or by the infusion of AHF plasma protein concentrate which has been extracted from the plasma of normal human whole blood. However, these techniques have often proved therapeutically unsatisfactory as will hereinafter appear.

When whole blood or blood plasma transfusions are used to relieve a hemophiliac, one must exercise great care to select reasonably fresh blood or plasma because the biologic activity of AHF is extremely labile upon storage under normal conditions. Even laboratory techniques, such as lyophilization and cryogenic preservation, will not prevent substantial loss of biologic activity of AHF over time. Another major disadvantage of whole blood or blood plasma transfusions is that they can introduce unwanted proteinaceous and non-proteinaceous material in the receipient's blood stream, often causing allergic reactions to sensitive patients, viral infections such as hepatitis, or hypervolumetric reactions to those persons who require extensive amounts of AHF to initiate clotting.

Another method of therapeutic technique, namely, i.v. administration of AHF plasma concentrate, is presently being used extensively. These concentrates are being developed primarily to circumvent the aforementioned troublesome and often times dangerous side effects caused by whole blood or plasma transfusions.

Essentially, AHF plasma concentrate might be characterized as AHF-rich blood plasma extracts from which some blood plasma proteins, such as the gamma globulins, most other blood plasma factors, and many inorganic chemicals have been removed. However, even currently available AHF-rich blood plasma concentrates may contain impurities which can cause deleterious effects when administered to man so that a need for a purer, more therapeutically acceptable AHF plasma concentrate still exists.

Of particular importance in the development of a more therapeutically acceptable AHF product has been the research directed towards the removal of fibrinogen from AHF plasma concentrate. Fibrinogen, contained in an AHF product, is an especially intolerable impurity because of its tendency to interfere with the blood platelets function of releasing essential clotting factors into the patients blood stream. Although the exact mechanism has not been conclusively determined, it now seems that the fibrinogen coats the cellular membrane of the platelet and inhibits the passage of the clotting factors from the platelet through its membrane into the blood plasma.

Another disadvantage arising from the presence of fibrinogen impurities in an AHF plasma concentrate is the tendency of fibrinogen to develop strong antigenic rejection responses in many patients who have been subjected to repeated and prolonged fibrinogen-rich AHF plasma concentrate infusions. It has also been medically shown that repeated massive doses of fibrinogen contained in an AHF plasma concentrate can cause the same antigenic response of the patient to become sensitive to other proteins in the AHF plasma concentrate, such as AHF, which might not normally be rejected if administered separately. Once anti-AHF antigens are formed within a patient, further therapeutic administration of AHF becomes less beneficial.

Because of the similar physical and chemical properties of AHF and fibrinogen, standard proteinaceous separation techniques, such as electrophoresis, chromatography, and solubility differentials, have not been able to effect a sharp separation of the two proteins to produce a therapeutically acceptable fibrinogen-free AHF product.

Accordingly, the need exists for a process whereby a low fibrinogen AHF plasma concentrate of high biologic activity might be derived from a biological sample containing a high concentration of fibrinogen.

2. Description of the Prior Art

Ethanol has been used for many years to precipitate human blood plasma proteins from solution. The prior art teaches that ethanol decreases the dielectric constant of the protein solvent and leads to a large decrease in solubility of the protein in the absence of a salt. Ethanol can also lead to protein denaturation unless the reaction is carried out at low temperatures, preferably below 0° C. E. J. Cohn and co-workers were the first to make use of these observations in the preparation of plasma protein fractions for therapeutic use. One of the contributions of E. J. Cohn and co-workers to the prior art was the precipitation of fibrinogen and AHF from human blood at very low ethanol concentrations (8 to 10% by volume) at temperatures between 0° C. and −3° C. and pH values near 7. (Cohn, E. J., Strong, L. E., Hughes, Jr., W. L., Mulford, D. J., Ashworth, J. N., Melin, M., and Taylor, H. L., *J. Amer. Chem. Soc.*, 68, 459, 1946). Ethanol precipitation of fibrinogen and antihemophilic factor from solution has been also utilized by others. For example: ethanol-glycine precipitates from plasma and solution (Blomback, B. and Blomback, M., *Arkiv F. Kemi.*, 10, 415, 1956, Blomback, M., *Arkiv F. Kemi.*, 12, 387, 1958); cryoprecipitate-ethanol precipitation from plasma (Newman, J., Johnson A. J., Karpatkin, M. H., Puszkin, S., *Brit. J. Haem.*, 21, 1, 1971); and ethanol precipitation of antihemophilic factor from solution (Hershgold, E. J., Pool, J. G., Pappenhagen, A. R., *J. Lab. & Clin. Med.*, 67, 23, 1966). Under the conditions described in these references antihemophilic factor and fibrinogen tend to co-precipitate and the main contaminant of the resultant antihemophilic factor concentrate is fibrinogen. In addition to the undesirable presence of fibrinogen in AHF preparations of the prior art the procedures used for preparing the same also suffer from drawbacks. The ethanol precipitation of fibrinogen and antihemophilic factor generally closely follows the Cohn fractionation rule of not allowing the solution temperature to rise above 0° C. during ethanol processing for fear of protein denaturation. Temperature control below 0° C. is especially difficult during ethanol addition to protein solutions because the reaction of ethanol and water is exothermic resulting in the liberation of a substantial quantity of heat. Thus, slow addition of ethanol and rapid mixing of the solution is required to maintain the temperature below 0° C. Even with such measures localized areas of the plasma solution may reach temperatures substantially above 0° C. resulting in protein denaturation.

Accordingly, it is the prime objective of this invention to provide a method for preparing a stable, high yield, low fibrinogen antihemophilic factor concentrate utilizing a warm ethanol technique.

This and further objects as shall hereinafter appear are achieved by the present invention in a remarkably unexpected fashion as will be discerned from the following description.

SUMMARY OF THE INVENTION

It has now been found that fibrinogen can be nearly completely separated from antihemophilic factor by ethanol precipitation with minimal impact on the antihemophilic factor yield at temperatures substantially above 0° C. The problem of protein heat denaturation, caused by adding ethanol to a protein solution, has been avoided by adding human plasma cryoprecipitate to a previously prepared ethanol-water solution. The antihemophilic factor concentrate produced thereby contains very low levels of fibrinogen, it is of high yield and stability and thus suitable for commercial production.

In accordance with the present invention the antihemophilic factor concentrate is prepared by a process comprising the steps of:
(a) suspending cryoprecipitate, obtained from human blood plasma, at room temperature in an ethanol-water solution containing up to 10% v/v ethanol to obtain a final solution of low ionic strength;
(b) adjusting the pH to about 6.0 to 6.8 and cooling the solution to about 5° to 15° C. to obtain a precipitate comprising fibrinogen and cold-insoluble globulins;
(c) adding a low concentration aluminum hydroxide solution to adsorb trace proteins, blood factors VII, IX, X and prothrombin;
(d) removing said aluminum hydroxide and adsorbed proteins and prothrombin from the solution;
(e) clarifying the solution by filtration;
(f) adjusting the pH of the solution to about 7.0;
(g) optionally removing the ethanol from the solution by diafiltration; and
(h) optionally adjusting the AHF potency of the solution by ultrafiltration.

The resultant solution is either used as the starting material for further purification or is subjected to sterile filtration. If the latter is desired, the filtrate obtained therefrom may be put directly into sterile vials or freeze-dried to form a sterile dry AHF preparation. The solution and dry preparations may be marketed directly as such.

DETAILED DESCRIPTION OF THE INVENTION

The starting material for obtaining AHF is frozen human blood plasma or any fraction thereof containing as its primary components AHF and fibrinogen. In addition, the starting material may be other biologic fractions, such as recombinant DNA broth fractions containing AHF and fibrinogen. The frozen plasma is allowed to partially thaw under controlled temperatures of 0° C. to 4° C., then crushed. The cryoprecipitate is then separated from the plasma by centrifugation at about 0° to 4° C. As used herein, the term cryoprecipitate defines the solid phase fraction of human plasma obtained as a result of thawing frozen human plasma to 0° to 4° C., and removing the liquid phase. This solid fraction contains as its primary components AHF, fibrinogen, and various cold-insoluble globular proteins.

The present invention is predicated upon the discovery of a process whereby AHF can be substantially extracted from fibrinogen and cold-insoluble components of the cryoprecipate without significant loss of AHF biologic activity.

The cryoprecipitate is dissolved at a temperature of about 22° to 28° C. in water-ethanol solution, containing up to 3 units of an anticoagulant such as sodium heparin, at a ratio of two to four parts solution to one part cryoprecipitate, which solution was previously made in order to avoid subjecting the cryoprecipitate to heat generated by the exothermic reaction of water and ethanol. The amount of ethanol present in the ethanol-water solution should not be more than about 10% v/v. It has been found that while effectiveness of fibrinogen removal increases with increasing concentration of ethanol present in the ethanol-water solution up to about 10% v/v of ethanol, further increase in ethanol concentration does not result in additional effectiveness. On the other hand, loss of AHF considerably increases with the use of water-ethanol solutions that contain more than 10% v/v ethanol. The water-ethanol solution may contain an anticoagulant, such as sodium heparin, of up to 3 units per ml.

Next, the mixture is adjusted to a pH of about 6.0 to 6.8 with a pharmaceutically acceptable acid, such as acetic acid, then cooled to about 5° to 15° C. and stirred continuously at this temperature for about 30 minutes. A precipitate containing mostly fibrinogen and the cold-insoluble globulins is formed during this stirring procedure.

Next with stirring 25 to 35 ml of sterile 2% aluminum hydroxide solution is added per liter of solution followed by centrifugation or filtration of the solution at 10° to 15° C. to obtain a precipitate which is then discarded. Centrifugation of the solution is accomplished at between 10,000 and 15,000 gravities for 10 to 30 minutes to effect sharp separation of the solid and liquid phases. The solid phase now consists primarily of fibrinogen and cold-insoluble globulin proteins. The liquid supernatant consists primarily of AHF and trace amounts of fibrinogen. The AHF rich supernatant is then further clarified by filtration or other equivalent means.

To the clarified AHF-rich solution a low molar concentration of sodium citrate, glycine and sodium chloride solution is added and its pH is adjusted to 7.0 with a pharmaceutically acceptable base, such as 0.5M sodium hydroxide.

Finally, the solution may optionally be subjected to ultrafiltration and/or diafiltration to remove ethanol and adjust the antihemophilic factor potency. The so-obtained aqueous AHF solution is either used as the starting material for further purification or subjected to sterile filtration. The filtrate obtained therefrom may be put directly into sterile vials or freeze-dried to form a sterile dry preparation.

If further purification is desired, prior to lyophilization the AHF rich supernatant may be processed by many standard laboratory techniques to produce a purer product, such as cold ethanol precipitation, ion exchange and affinity chromatography.

EXAMPLE 1

1200 liters of frozen human plasma was allowed to remain at 0° C. to 4° C. until partially thawed, and then crushed and brought to 0° C. to 2° C. by circulating water through the jacket of the vessel containing the plasma. The cyroprecipitate was then separated from the plasma by centrifugation at 0° C. to 2° C.

A solution containing water, 6% v/v ethanol and 3 $\mu$/ml sodium heparin was prepared. 12 kg of cryoprecipitate was dissolved in 34 kg of the ethanol-water-heparin solution at a temperature of about 25° C. The mixture was then adjusted to about pH 6.4 with 3 liter of 0.1 M acetic acid, cooled to about 10° C. and held with continuous stirring at this temperature for 30 minutes. 1.5 liter of sterile 2% aluminum hydroxide solution was then added and the mixture stirred for an additional 5 minutes. The solution was centrifuged at a temperature between 10° C. and 15° C. and the precipitate was discarded. The effluent was clarified by filtration. To 44 kg of solution was then added 73 g sodium chloride, 135 g glycine and 246 ml of a 1.5 M sodium citrate solution and the pH was adjusted to 7.0 with 80 ml of 0.5 M sodium hydroxide.

The solution was then sterile filtered and freeze-dried. The resultant AHF had a commercially acceptable potency and yield with a total protein specific activity of 1.3 IU/mg and a fibrinogen specific activity of 23.9 IU/mg.

EXAMPLE 2

500 liters of frozen plasma was allowed to remain at 0° C. to 4° C. until partially thawed and then crushed and brought to 0° C. to 2° C. by circulating water through the jacket of the vessel containing the plasma. The cryoprecipitate was then separated from the plasma by centrifugation at 0° C. to 2° C.

A solution containing water, 6% v/v ethanol and 3 $\mu$/ml sodium heparin was prepared. 6 kg of cryoprecipitate was dissolved in 16 kg of the ethanol-water-heparin solution at a temperature of about 25° C. The mixture was then adjusted to about pH 6.4 with 1.4 liter of 0.1 M acetic acid, cooled to about 10° C. and held with continuous stirring at this temperature for 30 minutes. 1.4 liter of sterile 2% aluminum hydroxide solution was then added and the mixture stirred for an additional 5 minutes. The solution was centrifuged at a temperature between 10° C. and 15° C. and the precipitate was discarded. The effluent was clarified by filtration. To 20 kg of solution was then added 33 g sodium chloride, 62 g glycine and 112 ml of a 1.5 M sodium citrate solution and the pH was adjusted to 7.0 with 88 ml of 0.5 M sodium hydroxide.

The resultant solution was diafiltered to remove ethanol and ultrafiltered to adjust the AHF potency. The diafiltered and ultrafiltered solution was adjusted to pH 7.0 with 0.5 M NaOH, sterile filtered and freeze-dried. The resultant AHF had a commercially acceptable potency and yield with a total protein specific activity of 1.0 IU/mg and a fibrinogen specific activity of 24.6 IU/mg.

In the Examples: fibrinogen was determined by a thrombin clotting assay; potency of AHF was determined by a two-stage thromboplastin generation test wherein AHF units are in International Units; and protein was determined by the biuret assay for total protein. From the result of the assays:

$$\text{Total Protein Specific Activity} = \frac{AHF \text{ Units/Vial}}{\text{mg Protein/Vial}} =$$

$$AHF \text{ Units/mg Total Protein};$$

$$\text{and Fibrinogen Specific Activity} = \frac{AHF \text{ Units/Vial}}{\text{mg Fibrinogen/Vial}} =$$

$$AHF \text{ Units/mg Fibrinogen}$$

Various modifications of the present invention will be apparent to those skilled in the art and may be made without departing from the spirit and scope thereof, and it is therefore to be understood that the invention is to be limited only by the scope of the appended claims.

What is claimed is:

1. A method for producing a substantially fibrinogen-free antihemophilic factor product from a human blood plasma fraction containing as its primary components antihemophilic factor and fibrinogen comprising:
   (a) suspending said human blood plasma fraction in a water-ethanol solution containing up to 10% v/v ethanol at room temperature to obtain a solution of low ionic strength;
   (b) adjusting the pH of the solution to about 6.0 to 6.8 and cooling the solution to about 5° to 15° C. to form a precipitate comprising fibrinogen and cold-insoluble globulins;

(c) adding a low concentration aluminum hydroxide solution to adsorb trace proteins, blood factors VII, IX, X and prothrombin;
(d) removing the precipitate and said aluminum hydroxide and adsorbed proteins and prothrombin from the solution;
(e) clarifying the solution; and
(f) adjusting the pH to about 7.0.

2. The method of claim 1 wherein said aluminum hydroxide solution has a concentration of about 2% v/w.

3. The method of claim 1 wherein said water-ethanol solution further comprises an anticoagulant.

4. The method of claim 3 wherein said anticoagulant is sodium heparin.

5. The method of claim 4 wherein said sodium heparin is present in said water-ethanol solution in a concentration not exceeding 3 units per ml of solution.

6. The method of claim 1 wherein said clarifying of the solution step is by filtration.

7. The method of claim 1 wherein removal of precipitate is by centrifugation.

8. The method of claim 1 wherein removal of precipitate is by filtration.

9. The method of claim 1 further comprising the step of removing the ethanol from the solution.

10. The method of claim 9 wherein said removal of ethanol is by lyophilization.

11. The methods of claim 9 wherein said removal of ethanol is by diafiltration.

12. The method of claim 9 further comprising the step of sterile filtering the solution.

13. The method of claim 12 wherein the sterile filtered solution is lyophilized.

14. A method for producing a substantially fibrinogen-free antihemophilic factor product from a cryoprecipitate containing as its primary components antihemophilic factor and fibrinogen comprising:
(a) suspending the cryoprecipitate in a 0.5 to 10.0% v/v ethanol 99.5 to 90.0% v/v water solution, said solution containing not more than 3 units of sodium heparin per ml of solution at a ratio of about 3 parts ethanol-water-sodium heparin solution to 1 part cryoprecipitate, at a temperature of 22° to 28° C.;
(b) adjusting the pH of the solution to about 6.4 and cooling the solution with stirring to 5° to 15° C. to form a precipitate comprising fibrinogen and cold-insoluble globulins;
(c) adding a low concentration aluminum hydroxide solution to adsorb trace proteins, blood factors VII, IX, X and prothrombin;
(d) removing the precipitate and adsorbed proteins formed in steps (b) and (c) and aluminum hydroxide by centrifugation to obtain an effluent;
(e) clarifying said effluent by filtration;
(f) adding physiologically desired amounts of sodium citrate, glycine and sodium chloride to the clarified effluent;
(g) adjusting the pH of said effluent to about 7.0; and
(h) removing the ethanol from said effluent.

15. The method of claim 14 further comprising the step of sterile filtering the effluent subsequent to step (h) to obtain a filtrate.

16. The method of claim 15 wherein said filtrate is lyophilized.

17. The method of claim 14 wherein the removal of ethanol is by ultrafiltration.

18. The method of claim 14 wherein the removal of ethanol is by diafiltration.

* * * * *